US007531335B1

(12) United States Patent
Hauer et al.

(10) Patent No.: US 7,531,335 B1
(45) Date of Patent: May 12, 2009

(54) MODIFIED CYTOCHROME P450 MONOOXYGENASES

(75) Inventors: Bernhard Hauer, Fußgönheim (DE); Juergen Pleiss, Asperg (DE); Ulrich Schwaneberg, Waiblingen (DE); Jutta Schmitt, Stuttgart (DE); Markus Fischer, Ludwigsburg (DE); Rolf Schmid, Stuttgart (DE); Qing-shan Li, Kyoto (JP)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/031,695

(22) PCT Filed: Jul. 27, 2000

(86) PCT No.: PCT/EP00/07252

§ 371 (c)(1),
(2), (4) Date: Jan. 23, 2002

(87) PCT Pub. No.: WO01/07574

PCT Pub. Date: Feb. 1, 2001

(30) Foreign Application Priority Data

Jul. 27, 1999 (DE) ............................... 199 35 115
Mar. 10, 2000 (DE) ............................... 100 11 723

(51) Int. Cl.
*C12N 9/02* (2006.01)
*C12N 15/00* (2006.01)
*C12N 1/20* (2006.01)
*C12P 7/00* (2006.01)
*C12P 21/04* (2006.01)
*C12Q 1/26* (2006.01)
*C07H 21/04* (2006.01)
*C12Q 1/00* (2006.01)
*C12Q 1/68* (2006.01)

(52) U.S. Cl. ............................ 435/189; 435/4; 435/6; 435/69.1; 435/71.1; 435/25; 435/132; 435/440; 435/252.3; 435/320.1; 536/23.2

(58) Field of Classification Search ................ 435/189, 435/440, 132, 252.3, 320.1, 25, 155, 4; 536/23.2, 536/23.7
See application file for complete search history.

(56) References Cited

FOREIGN PATENT DOCUMENTS

GB        2 294 692    5/1996
WO     WO 00/31273    6/2000

OTHER PUBLICATIONS

Li et al. "The Structure of the Cytochrome p450BM-3 haem domain complexed with fatty acid substrate, palmitoleic acid" Nature Structural Biology vol. 4 No. 2 (1997) pp. 140-146.

Modi et al. "The catalytic mechanism of cytochrome P450 BM3 involves a 6 Å movement of the bound substrate of reduction" Nature Structural Biology vol. 3 No. 5 (1996) pp. 414-417.
Ravichandran et al. "Crystal Structure of Hemoprotein Domain of P450BM-3, a Prototype for Microsomal P450's" Science vol. 261 (1993) pp. 731-736.
Schwaneberg et al. "A Continuous Spectrophotomeric Assay for P450 BM-3, a Fatty Acid Hydroxylating Enzyme, and its Mutant F87A$^1$" Analytical Biochemestry vol. 269 (1999) pp. 359-366.
Oliver et al. "A Single Mutation in Cytochrome P450 BM3 Changes Substrate Orientation in a Catalytic Intermediate and the Regiospecificity of Hyroxylation" Biochemistry vol. 36 (1997) pp. 1567-1572.
Schwaneberg et al. "P450 monooxyganase in Biotechnology I. Single-step, large scale purification method for cytochrome P450 BM-3 by anion-exchange chromatography" J. of Chromatography vol. 848 (1999) pp. 149-159.
Cherry et al. "Directed Evolution of a Fungal Peroxidase" Nature Biotechnology vol. 17 (1999) pp. 379-384.
Maves et al. "Decreased substrate affinity upon alteration of the substrate of the substrate-docking region in cytochrome $P450_{BM-3}$" FEBS Letters vol. 414 (1997) pp. 213-218.
Truan et al. "Thr268 in Substrate Binding and Catalysis in P450BM-3$^1$" Archives of Biochemistry and Biophysics vol. 349, (1998) pp. 53-64.
Yeom et al. "The Role of Thr268 in Oxygen Activation of Cytochrome $P450_{BM-3}$" Biochemistry vol. 34 (1995) pp. 14733-14740.
Klein et al. "Critical Residues Involved in FMN Binding and Catalytic Activity in Cytochrome $P450_{BM-3}$*" J. of Biological Chemistry vol. 268, No. 10 (1993) pp. 7553-7561.
Boddupalli et al. "Fatty Acid Monooxygenation by Cytochrome $P-450_{BM-3}$*" J. of Biological Chemistry vol. 206 No. 8, (1990) pp. 4233-4239.
Capdevila et al."The Highly Stereoselective Oxidation of Polyunsaturated Fatty Acids by Cytochrome P450BM-3*" J. of Biological Chemistry vol. 271 No. 37 (1996) pp. 22663-22671.
Graham-Lorence et al. "An Active Site Substitution, F87V, Converts Cytochrome P450 BM-3 into a Regio-and Stereoselective (14S, 15R)—Arachidonie Acid Epoxygeanse*" J. of Biological Chemistry vol. 272 No. 2, (1997) pp. 1127-1135.
Cleland et al. Protein Engineering (1996).
Kuchner et al. "Directed Evolution of Enzyme Catalysts" Tibtech vol. 15 (1997) pp. 523-530.
Stemmer "Rapid evolution of a protein in vitro by DNA shuffling" Nature vol. 370 (1994) pp. 389-391.
Bernstein et al. "The Protein Data Bank: A Computer-based Archival File for Macromolecular Structures" J. Mol. Biol. vol. 112 (1997) pp. 535-542.
Gerichtete Evolution von Enzymen, Bornscheuer, Angew Chem. 1998, 110, Nr. 22, 3285-3288.

*Primary Examiner*—Yong D Pak
(74) *Attorney, Agent, or Firm*—Novak Druce + Quigg LLP

(57) ABSTRACT

The present invention relates to modified cytochrome P450 monooxygenases with an altered substrate profile, to nucleic acid sequences coding therefor, to expression constructs and vectors, to recombinant microorganisms which comprise these vectors, and to processes for the microbiological production of terminally or subterminally hydroxylated aliphatic carboxylic acids.

5 Claims, 2 Drawing Sheets

Figure 2:
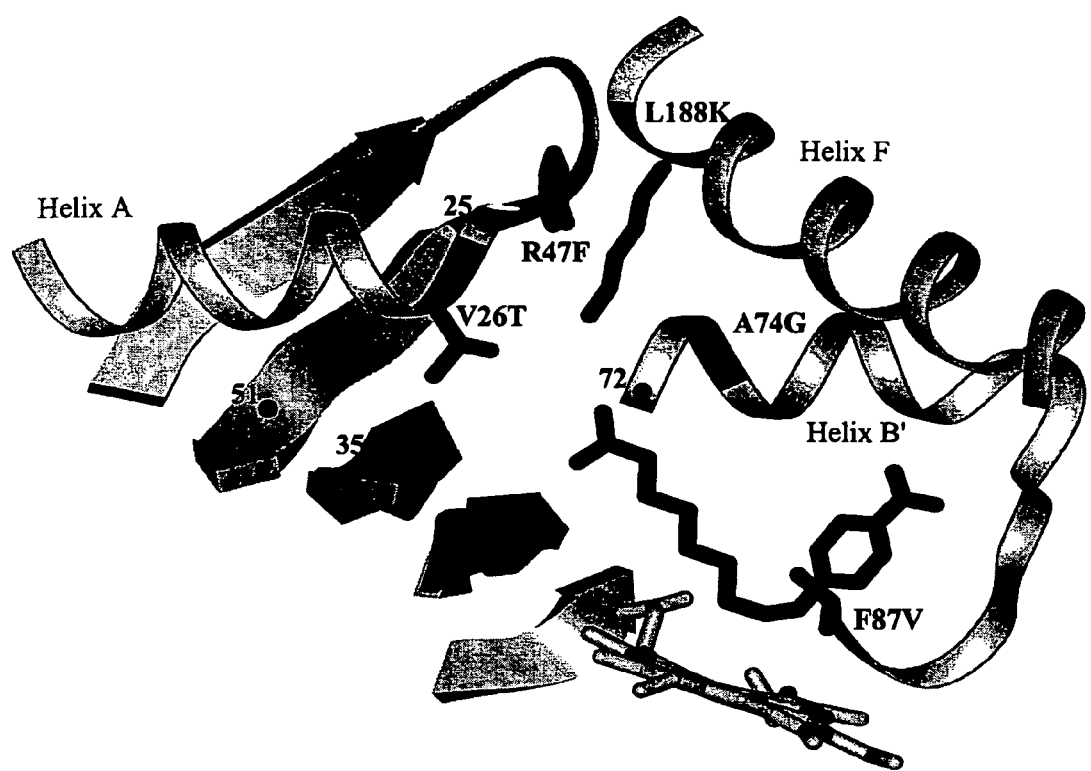

WT
↓
F87A

| F87A |

↓
L

| F87A |
| L188K |

↓
LA

| F87A |
| L188K |
| A74G |

↓
LAR

| F87A |
| L188K |
| A74G |
| R47F |

↓
LARV

| F87A |
| L188K |
| A74G |
| R47F |
| V26T |

↓
LARVF

| F87V |
| L188K |
| A74G |
| R47F |
| V26T |

Fig. 1

MODIFIED CYTOCHROME P450 MONOOXYGENASES

The present invention relates to modified cytochrome P450 monooxygenases with an altered substrate profile, to nucleic acid sequences coding therefor, to expression constructs and vectors, to recombinant microorganisms which comprise these vectors, and to processes for the microbiological production of terminally or subterminally hydroxylated aliphatic carboxylic acids.

The monooxygenase with the name P450 BM-3 is a cytochrome P450 enzyme from *Bacillus megaterium* and has a pronounced sequence homology with mammalian P450 enzymes (1). Owing to these correspondences, P450 BM-3 constitutes an excellent model system for this class of P450 enzymes. P450 BM-3 hydroxylates mainly long-chain saturated fatty acids on their ω-1, ω-2 and ω-3 carbon atom. Amides or alcohol analogs and epoxides of long-chain unsaturated fatty acids are also converted (1-3). The catalytic activity for saturated fatty acids depends on the chain length, the chain length optimum being 14 to 16 carbon atoms. The enzyme shows no catalytic activity for fatty acids with a chain length of less than 12 carbon atoms (1).

SUMMARY OF THE INVENTION

It is an object of the present invention to provide cytochrome P450 monooxygenase mutants which show a modified substrate profile in comparison with the wild-type enzyme. In particular, it was an object to provide novel mutants which hydroxylate saturated aliphatic carboxylic acids in another chain position and/or have a modified substrate specificity. In particular, it was an object to provide mutants which have a catalytic activity for aliphatic carboxylic acids of medium chain length, in particular with a chain length of 8 to 12, such as, for example, 8 to 10, carbon atoms, and which hydroxylate these carboxylic acids subterminally, especially at the positions ω-1, ω-2 and/or ω-3.

We have found that this object is achieved by providing modified cytochrome P450 monooxygenases which, owing to a combination of directed evolution and site-specific mutagenesis of their substrate-binding region, show an altered reactivity pattern or substrate profile in the terminal and/or subterminal enzymatic hydroxylation of aliphatic carboxylic acids in comparison with the wild type.

DETAILED DESCRIPTION OF THE INVENTION

Compared to the wild-type enzyme, an "altered substrate profile" is observed in mutants according to the invention. An "altered substrate profile" means, for the purposes of the present invention, a) an improved reactivity such as, for example, an increase in specific activity (expressed as nmol reacted carboxylic acid/minute/nmol P450-enzyme) and/or at least one kinetic parameter selected from amongst Kcat, Km and Kcat/Km, for example an improvement of at least 1%, such as, for example, 10 to 1000%, 10 to 500%, or 10 to 100%, of the mutant for at least one hydroxylatable aliphatic carboxylic acid or a hydroxylatable derivative of an aliphatic carboxylic acid, and/or b) an altered, in particular increased, regioselectivity in the hydroxylation of the carboxylic acid. There is thus, for example, a shift of the preferred terminal or subterminal (ω-1, ω-2, ω-3, ω-4, in particular ω-1 to ω-3) hydroxylation position at least one hydroxylatable carboxylic acid or a hydroxylatable derivative of an aliphatic carboxylic acid. Hydroxylatable aliphatic carboxylic acids or derivatives thereof in which an "altered substrate profile" can be observed in accordance with the invention are branched or, preferably, straight-chain carboxylic acids having 8 to 30 carbon atoms. The alteration according to the invention of the substrate profile may be manifested over the entire length (i.e. $C_8$-$C_{30}$) or only in sections, for example in the case of $C_8$-$C_{12}$—, $C_{10}$-$C_{12}$—, $C_{12}$-$C_{30}$—, $C_{12}$-$C_{25}$— or $C_{12}$-$C_{20}$ carboxylic acids or individual carboxylic acids from amongst these sections.

Nonlimiting examples which may be mentioned of carboxylic acids which can be hydroxylated in accordance with the invention are: caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotic acid and melissic acid. Examples of suitable carboxylic acid derivatives are $C_1$-$C_4$-alkyl esters, amides or anhydrides with, preferably, short-chain $C_1$-$C_4$-carboxylic acids.

The monooxygenases according to the invention are preferably derived from cytochrome P450 monooxygenases from the enzyme class E.C. 1.14.-.-, in particular from the P450 family CYP102, and are of eukaryotic or prokaryotic, in particular bacterial, origin.

An especially preferred group of mutants is derived from *Bacillus megaterium* cytochrome P450 monooxygenase BM-3 with an amino acid sequence as shown in SEQ ID NO:2, which has at least one functional mutation in one of the following amino acid sequence regions: 24-28, 45-51, 70-72, 73-82 (helix 5), 86-88 (helix 6), 172-224 (F/G loop) and 352-356 (β-strand 8), with the proviso that, if the enzyme carries the mutation F87A, more than one of these regions is mutated; and functional equivalents of these mutants.

In the present description, the mutation in question is shown in the amino acid one-letter code. The original amino acid is shown before the number which indicates the sequence position of the mutation, while the modified amino acid is shown after the number.

A "functional mutation" for the purposes of the present invention encompasses an amino acid exchange in the above-mentioned sequence regions which results in an "altered reactivity pattern" or "altered substrate profile" in accordance with the above definition.

Especially preferred in accordance with the invention are P450 BM-3 monooxygenase mutants (group (A)) which comprise individually or in combination in at least each case one functional mutation in the amino acid sequence regions 86-88, 172-224, 73-82, 45-51 and 24-28 (in accordance with SEQ ID NO: 2).

Thus, for example, Phe87 may be replaced by an amino acid with an aliphatic side chain such as, for example, Ala, Val, Leu, in particular Val or Ala; Leu188 may be replaced by an amino acid with an amine or amide side chain such as, for example, Asn, Gln, Arg or, in particular, Lys, or amino acids such as Ala, Gly, Ser and Trp; Ala74 may be replaced by another amino acid with an aliphatic side chain, such as, for example, Val and, in particular, Gly; Arg47 may be replaced by an amino acid with a cyclic side group such as, for example, His, Tyr or, in particular, Phe; and Val26 can be replaced by an amino acid with a hydroxyl side group such as, for example, Ser or, in particular, Thr.

Preferred group (A) mutants exhibit at least one of the following amino acid substitution patterns:

a) F87V;

b) F87A, L188K;

c) F87V, L188K;

d) F87A, L188K; A74G;

e) F87V, L188K, A74G;

f) F87A, L188K, A74G, R47F;

g) F87V, L188K, A74G, R47F;

h) F87A, L188K, A74G, R47F, V26T; or i) F87V, L188K, A74G, R47F, V26T;

and functional equivalents thereof.

A further group, group (B), of suitable mutants exhibits a single amino acid substitution in one of the abovementioned sequence regions or in one of the sequence regions 70-72 and 352-356. In the two last-mentioned sequence regions, Ser72, for example, may be replaced by an amino acid with an aliphatic side chain such as, for example, Ala, Val, Leu, Ile and, in particular, Gly, and Met354 may be replaced by an amino acid with a hydroxyl side group such as, for example, Ser or, in particular, Thr.

In particular, mutants of group B exhibit an amino acid substitution from amongst the following:

a) V26T, b) R47F, c) S72G, d) A74G, e) F87V, f) L188z, where z is K, R, W, Q, N, G, A or S, and g) M354T;

and functional equivalents thereof.

"Functional equivalents" are to be understood as meaning in accordance with the invention mutants which exhibit, in at least one of the abovementioned sequence positions, an amino acid substitution other than the one mentioned specifically, but still lead to a mutant which, like the mutant which has been mentioned specifically, show an "altered substrate profile" in accordance with the above definition over the wild type. Functional equivalence exists in particular also in the case where the alternations in the reactivity pattern correspond qualitatively.

"Functional equivalents" naturally also encompass P450 monooxygenase mutants which, like the P450 BM3 mutants which have been mentioned specifically, can be obtained by mutating P450 enzymes from other organisms. For example, regions of homologous sequence regions can be identified by sequence comparison. Following the principles of what has been set out specifically in the invention, the modern methods of molecular modeling then allow equivalent mutations to be carried out which affect the reaction pattern.

"Functional equivalents" also encompass the mutants which can be obtained by one or more additional amino acid additions, substitutions, deletions and/or inversions, it being possible for the abovementioned additional alterations to occur in any sequence position as long as they give rise to a mutant with an "altered substrate profile" in the above sense.

The present invention furthermore relates to nucleic acid sequences encoding a mutated monooxygenase or a "functional equivalent" in accordance with the above definition. These sequences can preferably be obtained from SEQ ID NO: 1 by codon exchange in accordance with the above amino acid substitution patterns.

The invention also encompasses those nucleic acid sequences which encompass so-called silent mutations or which are altered in comparison with a specifically mentioned sequence in accordance with the codon usage of a specific origin or host organism, and naturally occurring variants of such nucleic acid sequences. Also encompassed by the invention are deviations of the nucleic acid sequences obtained by the degeneracy of the genetic code (i.e. without altering the corresponding amino acid sequence) or by conservative nucleotide substitution (i.e. the corresponding amino acid is replaced by another amino acid with the same charge, size, polarity and/or solubility), and also sequences altered by the addition, insertion, inversion or deletion of nucleotides and which encode a monooxygenase according to the invention with an "altered substrate profile", and the corresponding complementary sequences.

The invention furthermore relates to expression constructs comprising a nucleic acid sequence encoding a mutant according to the invention under the genetic control of regulatory nucleic acid sequences; and vectors encompassing at least one of these expression constructs.

Preferably, the constructs according to the invention encompass a promoter 5'-upstream and a terminator sequence 3'-downstream of the encoding sequence in question, and, if appropriate, other customary regulatory elements, in each case operatively linked with the encoding sequence. Operative linkage is to be understood as meaning the sequential arrangement of promoter, encoding sequence, terminator and, if appropriate, other regulatory elements in such a manner that each of the regulatory elements can fulfill its intended function on expression of the encoding sequence. Examples of operatively linkable sequences are targeting sequences, or else translation enhancers, polyadenylation signals, selection markers, amplification signals, replication origins and the like.

In addition to the artificial regulatory sequences, the natural regulatory sequence can still be present upstream of the actual structural gene. If desired, this natural regulation may also be switched off by genetic alteration, and the expression of the genes may be enhanced or lowered. However, the gene construct may also be simpler in construction, i.e. no additional regulatory signals are inserted upstream of the structural gene and the natural promoter with its regulation is not removed. Instead, the natural regulatory sequence is mutated in such a way that regulation no longer takes place and the gene expression is increased or reduced. One or more copies of the nucleic acid sequences may be present in the gene construct.

Examples of promoters are: cos, tac, trp, tet, trp-tet, lpp, lac, lpp-lac, lacIq, T7, T5, T3, gal, trc, ara, SP6, l-PR or l-PL promoter, all of which are advantageously employed in Gram-negative bacteria; and the Gram-positive promoters amy and SPO2, the yeast promoters ADC1, MFa, AC, P-60, CYC1, GAPDH or the plant promoters CaMV/35S, SSU, OCS, lib4, usp, STLS1, B33, nos, or the ubiquitin or phaseolin promoter.

In principle, all natural promoters with their regulatory sequences can be used. In addition, synthetic promoters may also be used in an advantageous fashion.

The abovementioned regulatory sequences are intended to allow the directed expression of the nucleic acid sequences. Depending on the host organism, this may mean, for example, that the gene is expressed or overexpressed only after induction has taken placed, or that it is expressed and/or overexpressed immediately.

The regulatory sequences or factors can preferably have a positive effect on expression and in this manner increase or reduce the latter. Thus, an enhancement of the regulatory elements may advantageously take place at the transcriptional level by using strong transcription signals such as promoters and/or "enhancers". In addition, translation may also be enhanced by improving, for example, mRNA stability.

An expression cassette is generated by fusing a suitable promoter with a suitable monooxygenase nucleotide sequence and a terminator signal or polyadenylation signal. To this end, customary recombination and cloning techniques are used as they are described, for example, by T. Maniatis, E. F. Fritsch and J. Sambrook, Molecular Cloning: A Laboratory Manual, Cold Spring Harbor Laboratory, Cold Spring Harbor, N.Y. (1989) and by T. J. Silhavy, M. L. Berman and L. W. Enquist, Experiments with Gene Fusions, Cold Spring Harbor Laboratory, Cold Spring Harbor, N.Y. (1984) and by Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which allows optimal gene expression in the host. Vectors are well known to the skilled worker and can be found, for example, in "Cloning Vectors" (Pouwels P. H. et al., Ed., Elsevier, Amsterdam-N.Y.-Oxford, 1985). Vectors are to be understood as meaning not only plasmids, but all other vectors known to the skilled worker such as, for example, phages, viruses such as SV40, CMV, baculovirus and adenovirus, transposons, IS elements, phasmids, cosmids, and linear or circular DNA. These vectors can be replicated autonomously in the host organism or chromosomally.

The vectors according to the invention allow the generation of recombinant microorganisms which can be transformed, for example, with at least one vector according to the invention and which can be employed for producing the mutants. The above-described recombinant constructs according to the invention can advantageously be introduced into a suitable host system and expressed. It is preferred to use usual cloning and transfection methods known to the skilled worker, for example coprecipitation, protoplast fusion, electroporation, retroviral transfection and the like, in order to bring about expression of the abovementioned nucleic acids in the expression system in question. Suitable systems are described, for example, in Current Protocols in Molecular Biology, F. Ausubel et al., Ed., Wiley Interscience, New York 1997.

Suitable host organisms are, in principle, all organisms which allow expression of the nucleic acids according to the invention, their allelic variants, and their functional equivalents or derivatives. Host organisms are to be understood as meaning, for example, bacteria, fungi, yeasts or plant or animal cells. Preferred organisms are bacteria such as those of the genera *Escherichia* such as, for example, *Escherichia coli, Streptomyces, Bacillus* or *Pseudomonas*, eukaryotic microorganisms such as *Saccharomyces cerevisiae, Aspergillus*, and higher eukaryotic cells from animals or plants, for example Sf9 or CHO cells.

If desired, expression of the gene product may also be brought about in transgenic organisms such as transgenic animals such as, in particular, mice, sheep, or transgenic plants. The transgenic organisms may also be knock-out animals or plants in which the corresponding endogenous gene has been eliminated, such as, for example, by mutation or partial or complete deletion.

Successfully transformed organisms may be selected by means of marker genes which are also contained in the vector or in the expression cassette. Examples of such marker genes are genes for resistance to antibiotics and genes for enzymes which catalyze a color reaction causing the transformed cell to be colored. They may then be selected by means of automatic cell sorting. Microorganisms which have been transformed successfully with a vector and which carry a suitable gene for resistance to antibiotics (for example G418 or hygromycin) may be selected by suitable liquid or solid media containing antibiotics. Marker proteins presented on the cell surface may be exploited for selection by means of affinity chromatography.

The combination of the host organisms and the vectors which match the organisms, such as plasmids, viruses or phages, for example plasmids with the RNA polymerase/promoter system, the phages λ, μ or other temperate phages or transposons and/or further advantageous regulatory sequences, forms an expression system. The term "expression system" is to be understood as meaning, for example, the combination of mammalian cells, such as CHO cells, and vectors, such as pcDNA3neo vector, which are suitable for mammalian cells.

As described above, the gene product may advantageously also be expressed in transgenic animals, for example mice, sheep, or transgenic plants. Equally, it is possible to program cell-free translation systems with the RNA derived from the nucleic acid.

The invention relates furthermore to processes for the preparation of a monooxygenase according to the invention, in which a monooxygenase-producing microorganism is cultured, monooxygenase expression is induced, if appropriate, and the monooxygenase is isolated from the culture. In this manner, the monooxygenase according to the invention may also be produced on an industrial scale, if this is desired.

The microorganism can be cultured and fermented by known methods. Bacteria, for example, can be multiplied in TB or LB medium at a temperature of 20 to 40° C. and a pH of 6 to 9. Suitable culture conditions are described in detail for example by T. Maniatis, E. F. Fritsch and J. Sambrook, Molecular Cloning: A Laboratory Manual, Cold Spring Harbor Laboratory, Cold Spring Harbor, N.Y. (1989).

Unless the monooxygenase is secreted into the culture medium, the cells are then interrupted, and the monooxygenase is obtained from the lysate by known protein isolation methods. The cells may be disrupted as desired by high-frequency ultrasound, by high pressure, such as, for example, in a French pressure cell, by osmolysis, by the action of detergents, lytic enzymes or organic solvents, by homogenizers, or by combining a plurality of the methods listed.

The monooxygenase may be purified by known methods of chromatography, such as molecular sieve chromatography (gel filtration), such as chromatography on Q-Sepharose, ion-exchange chromatography and hydrophobic chromatography, and by other customary methods such as ultrafiltration, crystallization, salting out, dialysis and native gel electrophoresis. Suitable methods are described, for example, by Cooper, F. G., Biochemische Arbeitsmethoden [Methods in Biochemistry], Verlag Walter de Gruyter, Berlin, New York or by Scopes, R., Protein Purification, Springer Verlag, New York, Heidelberg, Berlin.

To isolate the recombinant protein, it is especially advantageous to use vector systems or oligonucleotides which extend the cDNA by certain nucleotide sequences and thus encode altered polypeptides or fusion proteins for the purposes of simpler purification. Such modifications which are suitable are, for example, tags which act as anchors, for example the modification known as hexa-histidine anchor or epitopes which can be recognized as antigens of antibodies (described, for example, by Harlow, E. and Lane, D., 1988, Antibodies: A Laboratory Manual. Cold Spring Harbor (N.Y.) Press). These anchors can serve to attach the proteins to a solid support such as, for example, a polymer matrix, which may be filled into a chromatography column or used on a microtiter plate or on any other carrier, for example.

At the same time, these anchors may also be used for recognizing the proteins. To recognize the proteins, it is additionally possible to use conventional labels, such as fluorescent dyes, enzyme labels which, after reaction with a substrate, form a detectable reaction product, or radiolabels, alone or in combination with the anchors for derivatizing the proteins.

The invention furthermore relates to biochemical processes for the enzymatic production of terminally or subterminally (ω-1 to ω-4) hydroxylated aliphatic carboxylic acids, which comprise a1) aerobically culturing a recombinant microorganism according to the invention in the presence of a culture medium which contains at least one hydroxylatable carboxylic acid or at least one hydroxylatable carboxylic acid derivative; or a2) aerobically incubating a reaction medium containing at least one hydroxylatable carboxylic acid or at least one hydroxylatable carboxylic acid derivative with a mutant according to the invention, and b) isolating the resulting hydroxylated product or product mixture from the medium.

The carboxylic acids can be employed in the process according to the invention per se or as derivatives thereof, such as, in particular, $C_1$-$C_4$-alkyl esters or carboxamides.

Hydroxylatable carboxylic acids which are preferably employed in the process according to the invention are $C_8$-$C_{30}$-monocarboxylic acids or derivatives thereof.

A hydroxylatable carboxylic acid which is especially preferably used in the process according to the invention is a $C_8$-$C_{12}$-monocarboxylic acid or a derivative thereof, and a monooxygenase which is especially preferably used in the process according to the invention is a mutant in accordance with the above group (A).

In accordance with another process according to the invention, the hydroxylatable carboxylic acid used is a $C_{12}$-$C_{30}$-monocarboxylic acid or a derivative thereof and the monooxygenase is a mutant selected from amongst the single mutants F87A, F87V, V26T, S72G, A74G and M354T, and the multiple mutants f) to i) in accordance with the above group (A).

The oxidation reaction according to the invention is usually carried out in the presence of atmospheric oxygen and in the presence of an electron donor (or reduction equivalent) such as, in particular, NADH, NADPH and Zn/Co(III) sepulchrate. The use of Zn/Co(III) sepulchrate is described, for example, in DE-A-199 35 115 which is herewith expressly referred to.

If the hydroxylation according to the invention is carried out with a recombinant microorganism, it is preferred first to culture the microorganisms in the presence of oxygen and in a complex medium such as, for example, TB or LB medium, at a cultivation temperature of approximately 20 to 40° C. and a pH of approximately 6 to 9 until a sufficient cell density is reached. Exogenous substrate is added as required. In order better to control the oxidation reaction, the use of an inducible, in particular a temperature-inducible, promoter is preferred. Here, the temperature is raised to the induction temperature required, for example 42° C. in the case of the $P_rP_1$ promoter, maintained over a sufficient period, for example 1 to 10 or 5 to 6 hours, to express the monooxygenase activity, and the temperature is then dropped to a value of approximately 30 to 40° C. Culturing is then continued for 12 hours to 3 days in the presence of oxygen.

If, in contrast, the oxidation according to the invention is carried out with purified or concentrated enzyme, the enzyme mutant according to the invention is dissolved in a medium comprising exogenous substrate (approximately 0.01 to 10 mM, or 0.05 to 5 mM), and the reaction is carried out, preferably in the presence of oxygen, at a temperature of approximately 10 to 50° C., such as, for example, 30 to 40° C., and a pH of approximately 6 to 9 (such as, for example, adjusted with 100 to 200 mM phosphate or Tris buffer), and in the presence of a reducing agent, during which process the substrate-comprising medium furthermore may exhibit an approximately 1 to 100-fold molar excess of reduction equivalents, based on the substrate to be oxidized. If required, the reducing agent may be added portionwise.

If required, oxygen may be passed into the reaction medium in a manner known per se.

If the processes according to the invention are carried out with enriched or purified enzyme, for example the following reaction conditions may be set:

| | |
|---|---|
| Substrate concentration: | 0.1 to 20 mg/ml |
| Enzyme concentration: | 0.1 to 10 mg/ml |
| Reaction temperature: | 20 to 40° C. |
| pH: | 6 to 8 |
| Buffer: | 0.05 to 0.2 M potassium phosphate, Tris/HCl |
| Electron donor: | is preferably added portionwise (initial concentration approx. 0.1 to 2 mg/ml). |

Before the reaction is started by adding the electron donor, it is possible to increase the activity by adding acetone in a concentration of 1 to 5% (v/v) and briefly preincubating (1 to 5 minutes at approximately 20 to 40° C.).

The skilled worker may deviate from these conditions and optimize the reaction conditions in question by routine experiments.

Two different strategies exist in protein engineering for generating variants with modified enzymatic properties: firstly, the "rational design" method (4), and secondly, the "directed evolution" method (5-7). Of central importance for successful rational design are a highly resolved three-dimensional structural model and an in-depth knowledge of the enzyme mechanism. While the rational design has been shown to generate enzyme mutants which have a high activity for unnatural substrates (4), the effect of individual amino acid point substitutions on stability, activity and specificity of the mutants can frequently not be predicted.

Even through X-ray structures of P450 BM-3 have been deposited in the protein database (8), the conformation of substrate and P450 during the critical hydroxylation stage remains unclear (9-11). Of central importance for the directed-evolution method is an efficient detection method for the rapid screening of large libraries of random mutants. An optical test for the P450 BM-3 mutant F87A, which employs ω-para-nitrophenoxycarboxylic acids (pNCA), has proved to be useful (12, 13). The single mutant F87A shifts the hydroxylation position of fatty acids from position ω-1, ω-2 and ω-3 towards the ω-position (13) and additionally leads to a complete conversion of 12-pNCA compared with a 33% conversion observed for the wild-type enzyme (12). However, since the monooxygenase domain of P450 BM-3 encompasses over 400 amino acids, the screening of a random-mutant library is like looking for a needle in a haystack.

To improve the efficiency of the searching procedure, the rational-design method was combined in accordance with the directed-evolution method so as to generate mutants with a modified reactivity, in particular for generating mutants with the specificity for fatty acids with medium chain length. The "rational evolution" method according to the invention is based on a computer-aided protein modeling to generate a virtual random library and to identify residues which are highly likely to affect the desired properties. A sublibrary is generated by randomizing these residues and screened for positive mutants. Starting from a structural model, the first step is the determination of residues which are potentially important for chain-length specificity. To generate mutants with improved properties, the mutation site proposed by the model is modified with the aid of the saturation mutagens. Then, the individual mutants with the best properties are combined with each other taking into consideration the rational design. The application of this combined strategy made it possible in particular to improve the activity of P450 BM-3 for substrates of medium chain length.

The application of this strategy and the sequence homology to P450 enzymes of different origins allow the skilled worker analogously to generate other mutants which are also the subject of the invention.

The present invention will now be illustrated by the following experiment description and taking into consideration the appended figures. The figures show:

FIG. 1: the stepwise optimization of P450 BM-3 for the new substrate 8-pNCA. The catalytic efficiency over 8-pNCA is shown for each mutant (in the unit $s^{-1}M^{-1}$); and FIG. 2: a model of the complex of the P450 BM-3-mutant LARVF with the substrate 8-pNCA. The side chains which show the five best positions for mutations and which were combined to give the mutant LARVF are shown (V26T, R47F, A74G, F87V, L188K).

METHOD 1

Modeling the Substrate/P450 BM-3 Complex

The modeling of the substrate/enzyme complex was based on the structure of P450 BM-3 which had been determined by crystallography, complexed with palmitoleic acid (9). This structure is deposited at the protein database (8). The crystal structure described, at a resolution of 2.9 Å, contains four molecules in an asymmetric unit cell. Chain A was selected as reference for the modeled complex. A model of 8-pNCA was generated as substrate molecule using the SYBYL "Molecule Builder" (Tripos, Inc., St. Louis, USA). The F87A mutation was generated using the SYBYL Biopolymer Tool. The carbon atoms 1 to 4 of the substrate were placed into the binding site matching the carbon atoms 6 to 9 of the bound palmitoleic acid. The torsion angle of the fatty acid chain was chosen in accordance with the transconfiguration step. NMR studies on P450 BM-3/laurate complexes and P450 BM-3/12-bromo-laurate complexes demonstrated that the protons of the hydroxylated carbon atoms (C10 and C11) are at an approximate distance of 3.0 Å from the heme iron, which is in the II oxidation state (10, 13). As a result of this finding, the corresponding atoms C7 and C8 of 8-pNCA were placed at a distance of 4 Å and 3.6 Å, respectively, from the heme iron. The para-nitrophenoxy group was arranged manually in the binding pocket. Also, the energy of the complex was minimized by fixed backbone atoms.

METHOD 2

Saturation Mutagenesis

The mutants used in accordance with the invention were generated with the aid of saturation mutagenesis using the Stratagene QuikChange Kit (La Jolla, Calif., USA). Nine positions in the vicinity of the substrate binding channel, viz. P25, V26, R47, Y51, S72, A74, F87, L188 and M354, were selected for mutation via P450 BM-3 modeling. The primers for each of these positions are compiled in Table 1.

TABLE 1

| Selected positions | Primers | Sequence No. |
|---|---|---|
| P25 | 5'-gttattaaacacagataaannngttcaagctttgatg-3' | SEQ ID NO: 9 |
|  | 5'-catcaaagcttgaacnnntttatctgtgtttaataac-3' | SEQ ID NO: 10 |
| V26 | 5'-gttattaaacacagataaaccgnnncaagctttgatg-3' | SEQ ID NO: 11 |
|  | 5'-catcaaagcttgnnncggtttatctgtgtttaataac-3' | SEQ ID NO: 12 |
| R47 | 5'-cgaggcgcctggtnnngtaacgcgctacttatc-3' | SEQ ID NO: 13 |
|  | 5'-gataagtagcgcgttacnnnaccaggcgcctcg-3' | SEQ ID NO: 14 |
| Y51 | 5'-cctggtcgtgtaacgcgcnnnttatcaagtcagc-3' | SEQ ID NO: 15 |
|  | 5'-gctgacttgataannngcgcgttacacgaccagg-3' | SEQ ID NO: 16 |
| S72 | 5'-gctttgataaaaacttannncaagcgcttaaatttgtacg-3' | SEQ ID NO: 17 |
|  | 5'-cgtacaaatttaagcgcttgnnnntaagtttttatcaaagc-3' | SEQ ID NO: 18 |
| A74 | 5'-gctttgataaaaacttaaagtcaannncttaaatttgtacg-3' | SEQ ID NO: 7 |
|  | 5'-cgtacaaatttaagnnnttgacttaagtttttatcaaagc-3' | SEQ ID NO: 8 |
| L188 | 5'-gaagcaatgaacaagnnncagcgagcaaatccag-3' | SEQ ID NO: 5 |
|  | 5'-ctggatttgctcgctgnnncttgttcattgcttc-3' | SEQ ID NO: 6 |
| M354 | 5'-ggcgacgaactannngttctgattcctcag-3' | SEQ ID NO: 19 |
|  | 5'-ctgaggaatcagaacnnntagttcgtcgcc-3' | SEQ ID NO: 20 |
| F87 | 5'-gcaggagacggggttgnnnacaagctggacg-3' | SEQ ID NO: 3 |
|  | 5'-cgtccagcttgtnnncaaccccgtctcctgc-3' | SEQ ID NO: 4 |

The reaction conditions were identical for all mutagenic PCR processes, with the exception of the annealing temperature, which was varied as follows: 50° C. for positions 25, 26, 188 and 354; 52° C. for positions 47 and 51; and 46° C. for positions 72, 74 and 87. The reactions were carried out in reaction volumes of 50 μl, each batch containing 17.5 pmol of each primer, 20 pmol of the template plasmid DNA, 3 U of the Pfu polymerase and 3.25 nmol of each dNTP. The reaction was started at 95° C., 4 minutes, and the batch then undergoes the following thermocycle 20 times: 95° C., 1 minute; 46-52° C., 2.5 minutes; 72° C., 17 minutes; after these 20 cycles, the reaction was continued for 15 minutes at 72° C. To carry out a site-specific mutagenesis by PCR, an individual codon was altered for exchanging one amino acid. To randomize a specific amino acid, primers were used in which "nnn" encodes the specific amino acid. All PCR product solutions were treated for 3 hours at 37° C. with 20 U DpnI to digest the original unmutated template DNA. Transformation into *E. coli* DH5α was then carried out.

METHOD 3

Expression and Purification of Wild-Type Enzyme and of the Mutants

The P450 BM-3 wild-type gene and its mutants wee expressed under the control of the strong temperature-inducible $P_RP_L$ promoter pCYTEXP1 into *E. coli* strain DH5α (supE44, lacU169 [80lacZ M15] hsdR17 recA1 endA1 gyrA96 thi-1 relA1). The single point mutation F87A was introduced in accordance with the prior art (12). The transformed cells were plated onto LB agar plates which contained 100 µg/ml ampicillin. After the colonies had grown for 12 to 24 hours, they were picked up with sterile toothpicks and placed into 96-well microtiter plates, each well containing 200 µl of TB medium (12 g tryptophan, 24 g yeast extract, 4 ml glycerol, (distilled) $H_2O$ to 1 liter) together with 100 µg/ml ampicillin. The plates were incubated overnight at 37° C. 40 µl were subsequently removed from each well and transferred into culture tubes which contained 2 ml TB medium with 100 µl/ml ampicillin, and the batches were subsequently incubated for 2 hours at 37° C. and then for 6 hours at 42° C. The cells were removed by centrifugation for 5 minutes at 4000 rpm, treated with chicken albumen lysozyme (1 U/ml), and then twice frozen and defrosted. The crude cell extracts were obtained by centrifugation for 10 minutes at 14,000 rpm. The activity was measured in the resulting supernatant. To produce large quantities of enzyme, a 2-1 shake flask with 300 ml of TB medium with 100 µl/ml ampicillin was used, incubated at 37° C., shaken for 2 hours at 200 rpm ($OD_{578nm}$=0.8 to 1.0) and subsequently incubated for 6 hours at 42° C. The cells were collected by centrifugation for 10 minutes at 4000 rpm and suspended in 15 ml of 0.1 M potassium phosphate buffer, pH 7.4. The ice-cooled suspension was disrupted with the aid of a Branson sonifier W25 (Dietzenbach, Germany) (80 W, 2 minutes, 3 cycles). The suspension was centrifuged for 20 minutes at 32570×g. The crude extracts were used for determining the enzyme activity or for enzyme purification.

Enzyme purification was carried out as described in (14), but using a BioPilot chromatography (Pharmacia, Sweden). Enzyme purity was determined by determining the total protein and the amount of enzyme. The concentration of purified enzyme was determined from the difference between the absorption spectrum of the carbonyl complex of the iron(II) form in comparison with the iron(II) form using a molecular absorptivity of 91 $mM^{-1}cm^{-1}$ for the wavelength pair 450 nm and 490 nm (1).

METHOD 4

Isolation of Mutants with Higher Activity for Substrates of Shorter Chain Length Instead of the wild type, the P450 BM-3 mutant F87A was used as template DNA. The mutations for the position in question were generated as described above. In each case approximately 100 colonies were picked for screening the sequence zone at each position and grown in culture tubes, and cells were isolated therefrom and lysed. The crude cell extracts from each selected colony were used for the activity test. All mutants which showed a higher activity than F87A for at least one substrate with a shorter chain length than 15-pNCA was sequenced for identifying the mutations.

The mutant with the highest activity for 12-pNCA, 10-pNCA or 8-pNCA, respectively, amongst all mutants for the same position was selected for a later combination with other mutations. The combined mutation was carried out stepwise by site-specific mutagenesis. The combinatory procedure is shown in FIG. 1. Six colonies were isolated from each combination step to determine the substrate specificity. A colony with a representative substrate specificity was selected, and the substrate specificity was determined for the pure enzyme. The plasmid of the selected colony was used for the next step of the site-specific mutagenesis. The mutations in the final mutant were identified by DNA sequencing (ABI PRISM® BigDye™ Terminator Cycle Sequencing Ready Reaction Kit and ABI Prism™ 377 DNA Sequencer).

METHOD 5

Enzyme Activity Assay

For the pNCA activity assay use was made of 8 µl of a 10 mM pNCA solution in DMSO in a disposable cell in an end volume of 1 ml. After 850 µl of Tris/HCl buffer (0.1 M, pH 8.2) and 0.1 to 0.4 nmol P450 had been added to the pNCA/DMSO solution in question, the samples were preincubated for 5 minutes before the reaction was started by adding 50 µl of an aqueous solution of 1 mN NADPH. To determine Kcat and Km, a concentration series was established for the various pNCA substrates (regarding details of the detection method, see (12)).

A 96-well plate (Greiner, Frickenhausen, Germany) was used for carrying out the pNCA test in a microtiter plate. In a total reaction volume of 250 µl in Tris/HCl buffer (0.1 M, pH 8.2), the reaction batch contained either 60 nmol 8-pNCA, 15 nmol 10-pNCA, 15 nmol 12-pNCA or 15 nmol 15-pNCA, in each case dissolved in 2.5 µl of DMSO. After the samples had been preincubated for 5 minutes with 40 µl of P450 BM-3 samples, the reaction was started by injecting, into each well, 30 µl of a 1 mM NADPH solution. Immediately after the NADPH solution had been added, the plates were measured in a plate reader at 405 nm.

METHOD 6

Conversion of Carboxylic Acids Using Mutants According a to the Invention, and Identification of the Products a) Chemical Reaction The following batch was chosen to hydroxylate the fatty acids in the presence of P450 BM-3 or its mutants:

| | | |
|---|---|---|
| P450 BM-3 mutant | 20 mg | |
| Reaction buffer | 20 ml | (Tris/HCl 50 mM, KCl 250 mM, pH 7.8) |
| Fatty acid | 10 mg | |
| Acetone | 400 µl | (2% v/v) (accelerates the reaction by a factor of 2) |

Prior to the reaction, the enzyme lyophilisate was dissolved in 1 ml of reaction buffer and first incubated for 30 minutes at 36° C. Like the addition of 2% v/v acetone, the incubation leads to an increase in activity of 60 and 75%, respectively.

After 5 minutes' incubation, 500 µl of the previously prepared NADPH solution (12.5 mg/ml) were added. The course of the reaction is monitored by absorption measurements at 340 nm, and the consumption of NADPH can be observed. Theoretically 4 ml of NADPH solution would be required for a stoichiometric conversion, however, an unduly high NADPH concentration in the reaction solution results in inactivation of the enzyme, which is why the cofactor is added in 500 µl steps.

After the reaction had ended, the solution was acidified with 5M hydrochloric acid to a pH of 2. The fatty acids or hydroxylated fatty acids precipitate during this and result in a noticeable cloudiness of the solution. Thereafter, the mixture was extracted twice with in each case 10 ml of dichloromethane and dried over sodium sulfate. After filtration through a folded filter, the dichloromethane was removed on a rotary evaporator or by evaporation with nitrogen. The white solid which remained was taken up in 2 ml of dichloromethane and used in the GC analysis.

b) Analysis by Gas Chromatography

A Fisons gas chromatograph (Fisons Instruments Mega Series, Mainz, Germany) equipped with FID was used for the analysis (Optima 5-column, internal diameter 25 m×0.25 mm, Macherey & Nagel, Duren, Germany).

For analysis, starting materials and products were silylated with MSHFBA. During this, all hydroxyl and acid groups are converted into the corresponding trimethylsilyl ethers and esters, respectively. Care must be taken that the sample is anhydrous since otherwise side reactions with the silylating agent result. 15 µl of MSHFBA were pipetted into 10 µl of the hydroxy-fatty-acid-containing dichloromethane solution and the mixture was incubated for 15 minutes at room temperature. After 25 µl of dichloromethane had been added, the GC analysis was carried out.

To this end, 1 µl of the silylated samples were injected into the gas chromatograph. Injector and detector temperature were 350° C. The following temperature programmes were used:

Caprylic acid 100° C. (2 min) $\xrightarrow{5°/min}$ 200° C. $\xrightarrow{10°/min}$ 300° C. (5 min)

Capric acid 100° C. (2 min) $\xrightarrow{5°/min}$ 140° C. (5 min) $\xrightarrow{10°/min}$ 300° C. (5 min)

Lauric acid 100° C. (2 min) $\xrightarrow{5°/min}$ 170° C. (5 min) $\xrightarrow{10°/min}$ 300° C. (5 min)

EXAMPLE 1

Selection of the Starting Mutant

The P450 BM-3 single mutant F87A was used as starting template. As already mentioned, this mutation shifts the hydroxylation position in saturated C12- and C14-fatty acids of ω-1, ω-2 and ω-3 towards the ω-position (13). For the conversion of 12-pNCA and 15-pNCA, it was also shown that the ω-hydroxylation is enhanced significantly over the wild type (12). As regards the ω-hydroxylation of 12-pNCA, a complete conversion was obtained compared with a 33% conversion in the case of the wild type. In addition to the increased regioselectivity, increased activities for 12-pNCA and 15-pNCA were also observed (compare Table 2).

TABLE 2

Specific activity of selected P450 BM-3 mutants for various pNCA derivatives with different chain lengths[1]

| Substrate | WT | F87A | L188K | V26T | R47F | S72G | A74G | M354T |
|---|---|---|---|---|---|---|---|---|
| 15-pNCA | 405 | 410 | 288 | 519 | 258 | 439 | 474 | 560 |
| 12-pNCA | 141 | 284 | 316 | 555 | 233 | 596 | 517 | 480 |
| 10-pNCA | 339 | 92 | 207 | 106 | 52 | 150 | 103 | 171 |
| 8-pNCA | 15 | 2 | 69 | 16 | 13 | 3 | 6 | 4 |

[1]Units of specific activity: nmol/min/nmol P450

The increased regioselectivity of F87A can be understood with reference to the structural model. The substitution of the bulky residue F87 by alanine enlarges the binding pocket for the p-nitrophenoxy group formed by F87, and also by V78, A82, T260, I263 and A264. In addition, the access of the large p-nitrophenoxy group to the binding pocket is facilitated and the steric interactions between F87 and the carbon atoms ω-2 and ω-1 of the pNCA are eliminated. This allows a more advantageous orientation of the ω-position relative to the heme iron atom.

EXAMPLE 2

Selection of Individual Mutation Positions by Modeling, Site-Specific Randomization Mutagenesis of Selected Positions, and Screening 1. Selection of the Mutation Positions The model of the bound C8-pNCA substrate shows that the carboxylate is at a distance of 9 and 11 Å from the carboxylate-binding residues R47 and Y51, respectively. To induce activity for C8 substrates, it is necessary to generate a new binding site which is at a suitable distance from the carboxylate group of the substrate. Additional residues should be positioned within the binding site to facilitate the binding of 8-pNCA. The following residues were selected: the residues R47 and Y51, which form the original carboxylate binding site. For R47, it is proposed to form an ion pair between its guanidinium group and the carboxylate residue of the substrate; Y51 forms a hydrogen bridge with the carboxylate group of the substrate (9). In the palmitoleic acid/P450 BM-3 complex, the distance between the $C_\alpha$ atom of R47 and the C atom of the fatty acid carboxylate group is 12 Å. All residues in the hemisphere with a 12 Å radius around the carboxylate group of the 8-pNCA model were identified, and only those were selected within the binding pocket which have side chains pointing towards the carboxylate group of the fatty acid. In this manner, P25, V26, S72, A74, L188 and M354 were selected, and these are probably capable of forming a new carboxylate binding site for short-chain pNCA compounds. These six selected residues are located on secondary structural elements with a flexible conformation (11).

2. Mutation and Screening

Mutants of each of the eight selected residues were generated by site-specific randomization of the wild-type codon at the positions in question. To ensure that most of the 19 possible amino acid species are tested, 100 colonies of each position were isolated, cultured and tested for activity (the probability that each amino acid is tested is thus greater than 95%, with the exception of a probability of 79% for tryptophan and methionin). The mutants with a higher activity value for at least one substrate with a shorter chain length than 15-pNCA were selected for sequencing for identifying the mutation(s).

It emerged that position 188 is relatively variable. Most of the 100 colonies showed activity for pNCA. From these, 37 colonies were selected in accordance with their activity for 8-pNCA. 16 different amino acid types inclusive of the wild type were detected. This result furthermore confirmed that the selection of 100 colonies was sufficient to ensure that most of the 20 amino acids which are possible can be tested. Amongst the 15 substitutions, substitutions K, R, W, Q, N, G, A and S significantly increased the catalytic activity for substrates of shorter chain lengths. The substitution of L by negatively charged amino acids led to an activity for 10-pNCA, 12-pNCA and 15-pNCA which was reduced by a factor of three to seven.

The remaining seven positions were randomized in a manner similar to position 188. 7 to 19 colonies were selected from each position for DNA sequencing for detecting the mutation(s). Most of these genes were either unmutated, or else the gene product showed reduced activity for substrates of shorter chain lengths (the tests were carried out with pure enzyme). In each case only one mutant of positions 26, 47, 74 and 354, two mutants of position 72 and no mutants of positions P25 and Y51 showed a higher activity for substrates of shorter chain length in comparison with 15-pNCA. The mutant with the highest activity for 8-pNCA in position 188 and position 72, and also single mutants of positions 26, 47, 74 and 354 were selected for a combination. These mutations, which are listed in the above Table 2, contain the following substitutions: V26T, R47F, S72G, A74G, L188K and M354T. In comparison with F87A, the specific activity for 8-pNCA was increased by the factor 0.5 to 33.5. Each of these mutations was combined stepwise with the original mutation F87A.

EXAMPLE 3

Multiple Mutants Generated by Stepwise Combination of Mutants, and their Screening 1. Mutant L (F87A, L188K)

The selection of the first mutant is critical since the combination of single mutants does not necessarily result in a cumulation of the individual effects. The wrong selection of the first mutation might lead towards an evolutionary pathway which does not result in an optimal multiple mutation. In the case of a large starting pool of single mutants, an enormous combinatory diversity is likely and, as a consequence, finding the desired multiple mutant is unlikely.

Two criteria favor the selection of mutant L as starting material: its increased activity for 8-pNCA compared with all other mutants (Table 2), and the changes in the enzyme/substrate interaction and the properties of the binding site. To verify these changes, structural models of the selected mutants were generated by replacing the side chains of the mutation positions with the aid of the SYBYL method. L188 is located on the C terminus of the α-helix F. This helix and the vicinal G helices experience the greatest shift by substrate binding (9). The model illustrates that the exchange of leucine for lysine leads to the formation of a novel putative carboxylate binding site. The distance between the amino group of K188 with the carboxylate residue of 8-pNCA is 6 Å and thus comparable with the distance of the carboxylate group of palmitoleic acid and of the guanidinium group from R47 (the original binding residue), which value has been determined experimentally. The distance between the guanidinium group of R47 and the carboxylate group of 8-pNCA is 11.4 Å. It can therefore be proposed that the ion-pair reactions between the carboxylate group of the substrate and K188 together with the hydroxylated C8 atom take place in a reactive distance to the heme iron atom.

The other five mutants were combined stepwise with mutant L by site-specific mutagenesis (compare FIG. 1). A structural model of the mutants selected was generated for each mutagenesis step. The effects, of the mutants generated, on substrate binding was studied with reference to this model, and, on this basis, a rational explanation for the optimized properties of the mutants and their combinations was proposed.

2. Mutant LA (F87A, L188K, A74G)

Catalytic efficiency over 8-pNCA was increased by introducing mutation A74G into mutant L. A74 is located on the N-terminus of the α-helix B'. Since the side chain of A74 sterically interacts with the amino group of K188, this interaction is eliminated by exchanging A74 for glycine, thus allowing a more advantageous orientation of the side chain relative to the carboxylate group of the substrate.

3. Mutant LAR (F87A, L188K, A74G, R47F)

The catalytic efficiency for 8-pNCA was successfully improved by introducing the additional mutation R47F. The mutation R47F had two possible effects. Phenylalanine hinders the original carboxylate binding and enlarges the hydrophobic section, which is exposed to the solvent, at the entrance of the binding channel formed by the residues F11, L14, L17, P18, P45 and A191 (compare FIG. 2). This hydrophobic section is particularly important for attaching the substrate (11).

4. Mutant LARV (F87A, L188K, A74G, R47F, V26T)

If the mutation M354T is added to mutant LAR, the Kcat value for 8-pCNA is reduced. M354T was therefore not involved in further combination experiments. However, if the mutation V26T is added to mutant LAR, the resulting mutant LARV shows a slightly higher Kcat value and a slightly lower Km value than LAR. The catalytic efficiency for 8-pNCA was increased. If, instead, mutation S72G is carried out in mutant LAR, the Kcat value of 8-pNCA was reduced. This is why mutant LARV was selected for further mutations.

V26 is located at the N-terminus of the α-helix A. The model suggests that T26 might assume the role of the original residue Y51 of the binding site and might stabilize the carboxylate group of the substrate by forming a hydrogen bridge. The distance between the hydroxyl group of T26 and the amino group of K188 is 6.9 Å. Compared with the original binding site, this distance is approximately 2 Å greater (4.8 Å between the hydroxyl group of Y51 and the guanidinium group of R47). It is therefore possible that the K188-containing F helix is subjected to further conformational alterations, owing to which 8-pNCA is retained deeper down in the binding region, and the distance between T26 and K188 is reduced.

5. Mutant LARVF (F87V, L188K, A74G, R47F, V26T)

It was possible to demonstrate that position 87 is of particular importance for the catalytic activity and the substrate specificity of the enzyme (3, 13). This is why mutant LARV was optimized in position 87 by site-specific randomized mutagenesis. Amongst 100 colonies, one mutant was obtained which exhibited a catalytic efficiency of $3.5*10^4$ $s^{-1}M^{-1}$ for 8-pNCA. The DNA sequence data revealed that alanine in position 87 was replaced by valine.

It is known from the crystal structure (11) and earlier experiments (3, 13) that R87 is important for the access of the substrate to the heme iron. The bulky para-nitrophenyl group of this substance made it necessary to increase the size of the binding site by exchanging phenylalanine for alanine. By exchanging A87 for valine, the contact of $C_\omega$ with the heme iron atom is improved, owing to steric interactions between the ether oxygen and the V87 side chain.

The data reveal that two key steps, F87A to L and LARV to LARVF, increased the catalytic efficiency for 8-pNCA. This raised the question as to whether the other mutations in mutant LARVF can be reversed without losing the activity for 8-pNCA. Mutants were therefore generated which contain mutation F87V instead of mutation F87A. These mutants have the following names:

1.) L7V with the mutations F87V L188K

2.) AL7V with the mutations F87V L188K A74G

3.) ARL7V with the mutations F87V L188K A74G R47F

The following results were obtained in the activity assays.

TABLE 3

Kinetic parameters of P450 BM-3 mutants for pNCA derivatives of different chain lengths, determined at pH 8.0 and 25 °C

| | $K_{cat}$ ($s^{-1}$) | | | $K_m$ (μM) | | | $K_{cat}/K_m$ ($s^{-1}M^{-1}$) | | |
|---|---|---|---|---|---|---|---|---|---|
| | 12 | 10 | 8 | 12 | 10 | 8 | 12 | 10 | 8 |
| F87V | 0.7 | 1.8 | — | 3.8 | 8.5 | — | $1.7 \cdot 10^5$ | $2.1 \cdot 10^5$ | — |
| L7V | 2.8 | 4.7 | — | 6.4 | 14.2 | — | $4.3 \cdot 10^5$ | $3.3 \cdot 10^5$ | — |
| AL7V | 2.2 | 5.9 | 4.3 | 15.1 | 22.7 | 197.6 | $1.4 \cdot 10^5$ | $2.6 \cdot 10^5$ | $2.0 \cdot 10^4$ |
| ARL7V | 1.4 | 5.5 | 3.9 | 8.9 | 17.5 | 41.4 | $1.7 \cdot 10^5$ | $3.1 \cdot 10^5$ | $9.3 \cdot 10^4$ |
| ARVLF | 1.4 | 7.2 | 0.2 | 12.3 | 44.8 | 6.5 | $9.2 \cdot 10^4$ | $1.6 \cdot 10^5$ | $3.5 \cdot 10^4$ |

The results show that mutant F87V and L7V show no measurable conversion for the substrate 8-pNCA. The results furthermore show that the quadruple mutant ARL7V shows an even better catalytic efficiency than the quintuple mutant ARVLF.

Moreover, mutants ARL7V and ARVLF show high activities for capric acid (C10), which is shorter by two carbon atoms than the shortest native fatty acid substrate of the wild-type enzyme. Moreover, ω-4-monohydroxylated products were observed when lauric acid (C12) is used as substrate, while the wild-type enzyme of P450 BM-3 is only active in the positions ω-1, ω-2 and ω-3.

EXAMPLE 4

Determination of the Preferred Hydroxylation Position for Carboxylic Acids of Different Chain Lengths and Various Mutants, and Comparison with the Wild-Type Enzyme The reaction batches are worked up and analyzed in accordance with the above-described method (6).

The results are compiled in Table 4 below.

TABLE 4

| Hydroxylation positions | Capric acid (C10) [%] | Lauric acid (C12) [%] |
|---|---|---|
| Wild type | | |
| ω-3 | — | 34 |
| ω-2 | — | 28 |
| ω-1 | — | 38 |
| Mutant L7V | | |
| ω-3 | — | 53 |
| ω-2 | — | 30 |
| ω-1 | — | 17 |
| Mutant F87V | | |
| ω-3 | — | 51 |
| ω-2 | — | 25 |
| ω-1 | — | 24 |
| Mutant AL7V | | |
| ω-3 | — | 28 |
| ω-2 | — | 54 |
| ω-1 | — | 18 |

TABLE 4-continued

| Hydroxylation positions | Capric acid (C10) [%] | Lauric acid (C12) [%] |
|---|---|---|
| Mutant ARL7V | | |
| ω-3 | 14 | 35 |
| ω-2 | 33 | 50 |
| ω-1 | 53 | 15 |
| Mutant ARVLF | | |
| ω-3 | 15 | 34 |
| ω-2 | 30 | 53 |
| ω-1 | 55 | 13 |

What is noticeable in the hydroxylation of lauric acid is that a change in regioselectivity first takes place during the transition from the wild type to P450 BM-3 F87V, which preferentially catalyzes an ω-3 hydroxylation, as is the case with P450 BM-3 L7V. During the transition to the triple mutant, the regioselectivity changes again; P450 BM-3 AL7V, P450 BM-3 ARL7V and P450 BM-3 ARVLF preferentially direct the hydroxylation to the ω-2 position.

All GC analyses demonstrate that capric acid is only converted by P450 BM-3 ARVLF and P450 BM-3 ARL7V, while a conversion of less than 1% is found in the other mutants. Both enzymes exhibit a virtually identical regioselectivity, with the ω-1 position being preferred.

To determine the reaction yields, gas chromatograms of standards were recorded. The starting material standard used was capric or lauric acid solution with dichloromethane as solvent (concentration 0.5 mg/ml). Owing to the FID detection method, it was not possible to simply compare the peak areas of starting materials and products with one another since molecules which have different structural and empirical formulae generate different ion fluxes upon combustion. These ion fluxes are not proportional to the quantitative ratio of starting material and product. The product standard used was therefore commercially available 10-hydroxycapric acid or 12-lauric acid. The empirical formulae of the standards and of the products are identical, and the structure only differs with regard to the position of the hydroxyl group, which is why approximately identical detectable ion fluxes can be assumed for identical quantities.

In the hydroxylations of capric acid with P450 BM-3 ARVLF and P450 BM-3 ARL7V catalysis, the cumulative product yields were 57% and 38%, respectively. In the hydroxylations of lauric acid, the yield was 51% for P450 BM-3 ARVLF catalysis and between 38% and 40% for all other mutants and for the wild type.

REFERENCES

1. Boddupalli, S. S., et al., (1990) J. Biol. Chem. 265, 4233-4239
2. Capdevila, J. H., et al., (1996) J. Biol. Chem. 271, 22663-22671
3. Graham-Lorence, S., et al., (1997) J. Biol. Chem. 272, 1127-1135
4. Cleland, J. L. and Craik, C. S., Eds. (1996) Protein Engineering: Principles and Practice, Wiley-Liss, New York
5. Kuchner, O. and Arnold, F. H., (1997) Trends Biotechnol. 15, 523-530
6. Stemmer, W. P. C. (1994) Nature (London) 370, 389-391
7. Bornscheuer, U. T., (1998) Angew. Chem. 110, 3285-3288

8. Bernstein, F. C., et al., (1977) J. Mol. Biol. 112, 525-542
9. Li, H. and Poulos, T. L. (1997) Nat. Structural Biol. 4, 140-146
10. Modi, S., et al., (1996) Nat. Structural Biol. 3, 414-417
11. Ravichandran, K. G., et al., (1993) Science 261, 731-736
12. Schwaneberg, U., et al., (1999) Anal. Biochem. 269, 359-366
13. Oliver, C. F., et al., (1997) Biochemistry, 36, 1567-1572
14. Schwaneberg, U., et al., J. Chromatography A, in press
15. Cherry, J. R., et al., (1999) Nature Biotechnology, 17, 379-384

We claim:

1. A process for the enzymatic production of subterminally hydroxylated aliphatic carboxylic acids, which comprises
   a1) culturing a recombinant microorganism which has been transformed with a vector which encompasses an expression construct comprising, under the genetic control of regulatory nucleic acid sequences, a sequence which encompasses a nucleic acid sequence encoding a modified monooxygenase having a modification in the amino acid sequence of SEQ ID NO:2, which modification consists of one functional mutation in each of amino acid sequence positions 87 and 188 and, optionally, at least one additional functional mutation in one of amino acid sequence positions 26, 47, 72, 74 and 354, wherein:
   Phe 87 is replaced by at Val, Ala or Leu;
   Leu 188 is replaced by Asn, Gln, Arg, Lys, Ala, Gly, Ser or Trp;
   Ala 74 is replaced by Val or Gly;
   Arg 47 is replaced by His, Tyr or Phe;
   Val 26 is replaced by Ser or Thr;
   Ser 72 is replaced by Ala, Leu, Ile or Gly; or,
   Met 354 is replaced by Ser or Thr,
   wherein the functional mutation in comparison with the wild-type enzyme, results in an altered activity or regioselectivity in the subterminal enzymatic hydroxylation of an aliphatic $C_8$-$C_{12}$-carboxylic acid, whereby culturing is performed in the presence of a culture medium which contains at least one hydroxylatable $C_8$-$C_{12}$-carboxylic acid or a derivative thereof, said derivative being selected from an alkyl ester, an amide or an anhydride of the at least one hydroxylatable $C_8$-$C_{12}$-carboxylic acid; or
   a2) incubating a reaction medium containing at least one hydroxylatable $C_8$-$C_{12}$-carboxylic acid or a derivative thereof, said derivative being selected from an alkyl ester, an amide or an anhydride of the at least one hydroxylatable $C_9$-$C_{12}$-carboxylic acid with a modified monooxygenase as defined above, and
   b) isolating the resulting hydroxylated products from the medium.

2. A method as claimed in claim 1, wherein the at least one hydroxylatable carboxylic acid is a $C_9$-$C_{12}$-monocarboxylic acid or the derivative thereof, and the monooxygenase comprises at least one of the following amino acid substitution patterns in SEQ ID NO:2:
   a) F87V;
   b) F87A and L188K;
   c) F87V and L188K;
   d) F87A, L188K and A74G;
   e) F87V, L188K and A74G;
   f) F87A, L188K, A74G and R47F;
   g) F87V, L188K, A74G and R47F;
   h) F87A, L188K, A74G, R47F and V26T; or
   i) F87V, L188K, A74G, R47F and V26T.

3. A method as claimed in claim 1, wherein the enzymatic production is carried out in the presence of an electron donor or a reduction equivalent.

4. A method as claimed in claim 3, wherein the electron donor or the reduction equivalent is selected from the group consisting of NADH, NADPH and Zn/CO(III) sepulchrate.

5. A process for the enzymatic production of subterminally hydroxylated aliphatic carboxylic acids, which comprises:
   A1) culturing a recombinant microorganism transformed with a vector comprising a nucleic acid sequence encoding a modified monooxygenase having a modification in the amino acid sequence of SEQ ID NO:2, which modification consists of one functional mutation in each of amino acid sequence positions 87 and 188 and, optionally, at least one additional functional mutation in one of amino acid sequence positions 26, 47, 72, 74 and 354, wherein:
   Phe 87 is replaced by at Val, Ala or Leu;
   Leu 188 is replaced by Asn, Gln, Arg, Lys, Ala, Gly, Ser or Trp;
   Ala 74 is replaced by Val or Gly;
   Arg 47 is replaced by His, Tyr or Phe;
   Val 26 is replaced by Ser or Thr;
   Ser 72 is replaced by Ala, Leu, Ile or Gly; or,
   Met 354 is replaced by Ser or Thr,
   wherein the functional mutation in comparison with the wild-type enzyme results in an altered activity or regioselectivity in the subterminal enzymatic hydroxylation of an aliphatic $C_9$-$C_{12}$-carboxylic acid, whereby culturing is performed in the presence of a culture medium which contains at least one hydroxylatable $C_8$-$C_{12}$-carboxylic acid or a derivative thereof, said derivative being selected from an alkyl ester, an amide or an anhydride of the at least one hydroxylatable $C_8$-$C_{12}$-carboxylic acid; or
   A2) incubating a reaction medium containing at least one hydroxylatable $C_8$-$C_{12}$-carboxylic acid or a derivative thereof, said derivative being selected from an alkyl ester, an amide or an anhydride of the at least one hydroxylatable $C_8$-$C_{12}$-carboxylic acid with a modified monooxygenase as defined above, and
   B) isolating the resulting hydroxylated products from the medium.

* * * * *

SEQUENCE LISTING

<160> NUMBER OF SEQ ID NOS: 20

<210> SEQ ID NO 1
<211> LENGTH: 3150
<212> TYPE: DNA
<213> ORGANISM: Bacillus megaterium
<220> FEATURE:
<221> NAME/KEY: CDS
<222> LOCATION: (4)..(3150)

<400> SEQUENCE: 1

```
atg aca att aaa gaa atg cct cag cca aaa acg ttt gga gag ctt aaa      48
    Thr Ile Lys Glu Met Pro Gln Pro Lys Thr Phe Gly Glu Leu Lys
      1               5                  10                  15 aat tta ccg tta tta aac aca gat aaa ccg gtt caa gct ttg atg aaa      96
Asn Leu Pro Leu Leu Asn Thr Asp Lys Pro Val Gln Ala Leu Met Lys
                 20                  25                  30 att gcg gat gaa tta gga gaa atc ttt aaa ttc gag gcg cct ggt cgt     144
Ile Ala Asp Glu Leu Gly Glu Ile Phe Lys Phe Glu Ala Pro Gly Arg
             35                  40                  45 gta acg cgc tac tta tca agt cag cgt cta att aaa gaa gca tgc gat     192
Val Thr Arg Tyr Leu Ser Ser Gln Arg Leu Ile Lys Glu Ala Cys Asp
         50                  55                  60 gaa tca cgc ttt gat aaa aac tta agt caa gcg ctt aaa ttt gta cgt     240
Glu Ser Arg Phe Asp Lys Asn Leu Ser Gln Ala Leu Lys Phe Val Arg
     65                  70                  75 gat ttt gca gga gac ggg tta ttt aca agc tgg acg cat gaa aaa aat     288
Asp Phe Ala Gly Asp Gly Leu Phe Thr Ser Trp Thr His Glu Lys Asn
 80                  85                  90                  95 tgg aaa aaa gcg cat aat atc tta ctt cca agc ttc agt cag cag gca     336
Trp Lys Lys Ala His Asn Ile Leu Leu Pro Ser Phe Ser Gln Gln Ala
                100                 105                 110 atg aaa ggc tat cat gcg atg atg gtc gat atc gcc gtg cag ctt gtt     384
Met Lys Gly Tyr His Ala Met Met Val Asp Ile Ala Val Gln Leu Val
            115                 120                 125 caa aag tgg gag cgt cta aat gca gat gag cat att gaa gta ccg gaa     432
Gln Lys Trp Glu Arg Leu Asn Ala Asp Glu His Ile Glu Val Pro Glu
        130                 135                 140 gac atg aca cgt tta acg ctt gat aca att ggt ctt tgc ggc ttt aac     480
Asp Met Thr Arg Leu Thr Leu Asp Thr Ile Gly Leu Cys Gly Phe Asn
    145                 150                 155 tat cgc ttt aac agc ttt tac cga gat cag cct cat cca ttt att aca     528
Tyr Arg Phe Asn Ser Phe Tyr Arg Asp Gln Pro His Pro Phe Ile Thr
160                 165                 170                 175 agt atg gtc cgt gca ctg gat gaa gca atg aac aag ctg cag cga gca     576
Ser Met Val Arg Ala Leu Asp Glu Ala Met Asn Lys Leu Gln Arg Ala
                180                 185                 190 aat cca gac gac cca gct tat gat gaa aac aag cgc cag ttt caa gaa     624
Asn Pro Asp Asp Pro Ala Tyr Asp Glu Asn Lys Arg Gln Phe Gln Glu
            195                 200                 205 gat atc aag gtg atg aac gac cta gta gat aaa att att gca gat cgc     672
Asp Ile Lys Val Met Asn Asp Leu Val Asp Lys Ile Ile Ala Asp Arg
        210                 215                 220
```

```
aaa gca agc ggt gaa caa agc gat gat tta tta acg cat atg cta aac      720
Lys Ala Ser Gly Glu Gln Ser Asp Asp Leu Leu Thr His Met Leu Asn
    225                 230                 235 gga aaa gat cca gaa acg ggt gag ccg ctt gat gac gag aac att cgc      768
Gly Lys Asp Pro Glu Thr Gly Glu Pro Leu Asp Asp Glu Asn Ile Arg
240                 245                 250                 255 tat caa att att aca ttc tta att gcg gga cac gaa aca aca agt ggt      816
Tyr Gln Ile Ile Thr Phe Leu Ile Ala Gly His Glu Thr Thr Ser Gly
                260                 265                 270 ctt tta tca ttt gcg ctg tat ttc tta gtg aaa aat cca cat gta tta      864
Leu Leu Ser Phe Ala Leu Tyr Phe Leu Val Lys Asn Pro His Val Leu
            275                 280                 285 caa aaa gca gca gaa gaa gca gca cga gtt cta gta gat cct gtt cca      912
Gln Lys Ala Ala Glu Glu Ala Ala Arg Val Leu Val Asp Pro Val Pro
        290                 295                 300 agc tac aaa caa gtc aaa cag ctt aaa tat gtc ggc atg gtc tta aac      960
Ser Tyr Lys Gln Val Lys Gln Leu Lys Tyr Val Gly Met Val Leu Asn
    305                 310                 315 gaa gcg ctg cgc tta tgg cca act gct cct gcg ttt tcc cta tat gca     1008
Glu Ala Leu Arg Leu Trp Pro Thr Ala Pro Ala Phe Ser Leu Tyr Ala
320                 325                 330                 335 aaa gaa gat acg gtg ctt gga gga gaa tat cct tta gaa aaa ggc gac     1056
Lys Glu Asp Thr Val Leu Gly Gly Glu Tyr Pro Leu Glu Lys Gly Asp
                340                 345                 350 gaa cta atg gtt ctg att cct cag ctt cac cgt gat aaa aca att tgg     1104
Glu Leu Met Val Leu Ile Pro Gln Leu His Arg Asp Lys Thr Ile Trp
            355                 360                 365 gga gac gat gtg gaa gag ttc cgt cca gag cgt ttt gaa aat cca agt     1152
Gly Asp Asp Val Glu Glu Phe Arg Pro Glu Arg Phe Glu Asn Pro Ser
        370                 375                 380 gcg att ccg cag cat gcg ttt aaa ccg ttt gga aac ggt cag cgt gcg     1200
Ala Ile Pro Gln His Ala Phe Lys Pro Phe Gly Asn Gly Gln Arg Ala
    385                 390                 395 tgt atc ggt cag cag ttc gct ctt cat gaa gca acg ctg gta ctt ggt     1248
Cys Ile Gly Gln Gln Phe Ala Leu His Glu Ala Thr Leu Val Leu Gly
400                 405                 410                 415 atg atg cta aaa cac ttt gac ttt gaa gat cat aca aac tac gag ctg     1296
Met Met Leu Lys His Phe Asp Phe Glu Asp His Thr Asn Tyr Glu Leu
                420                 425                 430 gat att aaa gaa act tta acg tta aaa cct gaa ggc ttt gtg gta aaa     1344
Asp Ile Lys Glu Thr Leu Thr Leu Lys Pro Glu Gly Phe Val Val Lys
            435                 440                 445 gca aaa tcg aaa aaa att ccg ctt ggc ggt att cct tca cct agc act     1392
Ala Lys Ser Lys Lys Ile Pro Leu Gly Gly Ile Pro Ser Pro Ser Thr
        450                 455                 460 gaa cag tct gct aaa aaa gta cgc aaa aag gca gaa aac gct cat aat     1440
Glu Gln Ser Ala Lys Lys Val Arg Lys Lys Ala Glu Asn Ala His Asn
    465                 470                 475 acg ccg ctg ctt gtg cta tac ggt tca aat atg gga aca gct gaa gga     1488
Thr Pro Leu Leu Val Leu Tyr Gly Ser Asn Met Gly Thr Ala Glu Gly
480                 485                 490                 495 acg gcg cgt gat tta gca gat att gca atg agc aaa gga ttt gca ccg     1536
Thr Ala Arg Asp Leu Ala Asp Ile Ala Met Ser Lys Gly Phe Ala Pro
                500                 505                 510 cag gtc gca acg ctt gat tca cac gcc gga aat ctt ccg cgc gaa gga     1584
Gln Val Ala Thr Leu Asp Ser His Ala Gly Asn Leu Pro Arg Glu Gly
            515                 520                 525 gct gta tta att gta acg gcg tct tat aac ggt cat ccg cct gat aac     1632
Ala Val Leu Ile Val Thr Ala Ser Tyr Asn Gly His Pro Pro Asp Asn
```

-continued

```
          530                 535                 540
gca aag caa ttt gtc gac tgg tta gac caa gcg tct gct gat gaa gta    1680
Ala Lys Gln Phe Val Asp Trp Leu Asp Gln Ala Ser Ala Asp Glu Val
545                 550                 555 aaa ggc gtt cgc tac tcc gta ttt gga tgc ggc gat aaa aac tgg gct    1728
Lys Gly Val Arg Tyr Ser Val Phe Gly Cys Gly Asp Lys Asn Trp Ala
560                 565                 570                 575 act acg tat caa aaa gtg cct gct ttt atc gat gaa acg ctt gcc gct    1776
Thr Thr Tyr Gln Lys Val Pro Ala Phe Ile Asp Glu Thr Leu Ala Ala
                580                 585                 590 aaa ggg gca gaa aac atc gct gac cgc ggt gaa gca gat gca agc gac    1824
Lys Gly Ala Glu Asn Ile Ala Asp Arg Gly Glu Ala Asp Ala Ser Asp
                    595                 600                 605 gac ttt gaa ggc aca tat gaa gaa tgg cgt gaa cat atg tgg agt gac    1872
Asp Phe Glu Gly Thr Tyr Glu Glu Trp Arg Glu His Met Trp Ser Asp
                610                 615                 620 gta gca gcc tac ttt aac ctc gac att gaa aac agt gaa gat aat aaa    1920
Val Ala Ala Tyr Phe Asn Leu Asp Ile Glu Asn Ser Glu Asp Asn Lys
625                 630                 635 tct act ctt tca ctt caa ttt gtc gac agc gcc gcg gat atg ccg ctt    1968
Ser Thr Leu Ser Leu Gln Phe Val Asp Ser Ala Ala Asp Met Pro Leu
640                 645                 650                 655 gcg aaa atg cac ggt gcg ttt tca acg aac gtc gta gca agc aaa gaa    2016
Ala Lys Met His Gly Ala Phe Ser Thr Asn Val Val Ala Ser Lys Glu
                660                 665                 670 ctt caa cag cca ggc agt gca cga agc acg cga cat ctt gaa att gaa    2064
Leu Gln Gln Pro Gly Ser Ala Arg Ser Thr Arg His Leu Glu Ile Glu
                675                 680                 685 ctt cca aaa gaa gct tct tat caa gaa gga gat cat tta ggt gtt att    2112
Leu Pro Lys Glu Ala Ser Tyr Gln Glu Gly Asp His Leu Gly Val Ile
                690                 695                 700 cct cgc aac tat gaa gga ata gta aac cgt gta aca gca agg ttc ggc    2160
Pro Arg Asn Tyr Glu Gly Ile Val Asn Arg Val Thr Ala Arg Phe Gly
705                 710                 715 cta gat gca tca cag caa atc cgt ctg gaa gca gaa gaa gaa aaa tta    2208
Leu Asp Ala Ser Gln Gln Ile Arg Leu Glu Ala Glu Glu Glu Lys Leu
720                 725                 730                 735 gct cat ttg cca ctc gct aaa aca gta tcc gta gaa gag ctt ctg caa    2256
Ala His Leu Pro Leu Ala Lys Thr Val Ser Val Glu Glu Leu Leu Gln
                740                 745                 750 tac gtg gag ctt caa gat cct gtt acg cgc acg cag ctt cgc gca atg    2304
Tyr Val Glu Leu Gln Asp Pro Val Thr Arg Thr Gln Leu Arg Ala Met
                755                 760                 765 gct gct aaa acg gtc tgc ccg ccg cat aaa gta gag ctt gaa gcc ttg    2352
Ala Ala Lys Thr Val Cys Pro Pro His Lys Val Glu Leu Glu Ala Leu
                770                 775                 780 ctt gaa aag caa gcc tac aaa gaa caa gtg ctg gca aaa cgt tta aca    2400
Leu Glu Lys Gln Ala Tyr Lys Glu Gln Val Leu Ala Lys Arg Leu Thr
785                 790                 795 atg ctt gaa ctg ctt gaa aaa tac ccg gcg tgt gaa atg aaa ttc agc    2448
Met Leu Glu Leu Leu Glu Lys Tyr Pro Ala Cys Glu Met Lys Phe Ser
800                 805                 810                 815 gaa ttt atc gcc ctt ctg cca agc ata cgc ccg cgc tat tac tcg att    2496
Glu Phe Ile Ala Leu Leu Pro Ser Ile Arg Pro Arg Tyr Tyr Ser Ile
                820                 825                 830 tct tca tca cct cgt gtc gat gaa aaa caa gca agc atc acg gtc agc    2544
Ser Ser Ser Pro Arg Val Asp Glu Lys Gln Ala Ser Ile Thr Val Ser
                835                 840                 845 gtt gtc tca gga gaa gcg tgg agc gga tat gga gaa tat aaa gga att    2592
```

```
Val Val Ser Gly Glu Ala Trp Ser Gly Tyr Gly Glu Tyr Lys Gly Ile
            850                 855                 860 gcg tcg aac tat ctt gcc gag ctg caa gaa gga gat acg att acg tgc    2640
Ala Ser Asn Tyr Leu Ala Glu Leu Gln Glu Gly Asp Thr Ile Thr Cys
865                 870                 875 ttt att tcc aca ccg cag tca gaa ttt acg ctg cca aaa gac cct gaa    2688
Phe Ile Ser Thr Pro Gln Ser Glu Phe Thr Leu Pro Lys Asp Pro Glu
880                 885                 890                 895 acg ccg ctt atc atg gtc gga ccg gga aca ggc gtc gcg ccg ttt aga    2736
Thr Pro Leu Ile Met Val Gly Pro Gly Thr Gly Val Ala Pro Phe Arg
                900                 905                 910 ggc ttt gtg cag gcg cgc aaa cag cta aaa gaa caa gga cag tca ctt    2784
Gly Phe Val Gln Ala Arg Lys Gln Leu Lys Glu Gln Gly Gln Ser Leu
            915                 920                 925 gga gaa gca cat tta tac ttc ggc tgc cgt tca cct cat gaa gac tat    2832
Gly Glu Ala His Leu Tyr Phe Gly Cys Arg Ser Pro His Glu Asp Tyr
        930                 935                 940 ctg tat caa gaa gag ctt gaa aac gcc caa agc gaa ggc atc att acg    2880
Leu Tyr Gln Glu Glu Leu Glu Asn Ala Gln Ser Glu Gly Ile Ile Thr
    945                 950                 955 ctt cat acc gct ttt tct cgc atg cca aat cag ccg aaa aca tac gtt    2928
Leu His Thr Ala Phe Ser Arg Met Pro Asn Gln Pro Lys Thr Tyr Val
960                 965                 970                 975 cag cac gta atg gaa caa gac ggc aag aaa ttg att gaa ctt ctt gat    2976
Gln His Val Met Glu Gln Asp Gly Lys Lys Leu Ile Glu Leu Leu Asp
                980                 985                 990 caa gga gcg cac ttc tat att tgc gga gac gga agc caa atg gca cct    3024
Gln Gly Ala His Phe Tyr Ile Cys Gly Asp Gly Ser Gln Met Ala Pro
            995                 1000                1005 gcc gtt gaa gca acg ctt atg aaa agc tat gct gac gtt cac caa gtg    3072
Ala Val Glu Ala Thr Leu Met Lys Ser Tyr Ala Asp Val His Gln Val
        1010                1015                1020 agt gaa gca gac gct cgc tta tgg ctg cag cag cta gaa gaa aaa ggc    3120
Ser Glu Ala Asp Ala Arg Leu Trp Leu Gln Gln Leu Glu Glu Lys Gly
    1025                1030                1035 cga tac gca aaa gac gtg tgg gct ggg taa                            3150
Arg Tyr Ala Lys Asp Val Trp Ala Gly
1040                1045

<210> SEQ ID NO 2
<211> LENGTH: 1048
<212> TYPE: PRT
<213> ORGANISM: Bacillus megaterium

<400> SEQUENCE: 2

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
                20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110
```

-continued

```
Lys Gly Tyr His Ala Met Met Val Asp Ile Ala Val Gln Leu Val Gln
            115                 120                 125
Lys Trp Glu Arg Leu Asn Ala Asp Glu His Ile Glu Val Pro Glu Asp
        130                 135                 140
Met Thr Arg Leu Thr Leu Asp Thr Ile Gly Leu Cys Gly Phe Asn Tyr
145                 150                 155                 160
Arg Phe Asn Ser Phe Tyr Arg Asp Gln Pro His Pro Phe Ile Thr Ser
                165                 170                 175
Met Val Arg Ala Leu Asp Glu Ala Met Asn Lys Leu Gln Arg Ala Asn
            180                 185                 190
Pro Asp Asp Pro Ala Tyr Asp Glu Asn Lys Arg Gln Phe Gln Glu Asp
        195                 200                 205
Ile Lys Val Met Asn Asp Leu Val Asp Lys Ile Ile Ala Asp Arg Lys
210                 215                 220
Ala Ser Gly Glu Gln Ser Asp Asp Leu Leu Thr His Met Leu Asn Gly
225                 230                 235                 240
Lys Asp Pro Glu Thr Gly Glu Pro Leu Asp Asp Glu Asn Ile Arg Tyr
                245                 250                 255
Gln Ile Ile Thr Phe Leu Ile Ala Gly His Glu Thr Thr Ser Gly Leu
            260                 265                 270
Leu Ser Phe Ala Leu Tyr Phe Leu Val Lys Asn Pro His Val Leu Gln
        275                 280                 285
Lys Ala Ala Glu Glu Ala Ala Arg Val Leu Val Asp Pro Val Pro Ser
290                 295                 300
Tyr Lys Gln Val Lys Gln Leu Lys Tyr Val Gly Met Val Leu Asn Glu
305                 310                 315                 320
Ala Leu Arg Leu Trp Pro Thr Ala Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Leu Met Val Leu Ile Pro Gln Leu His Arg Asp Lys Thr Ile Trp Gly
        355                 360                 365
Asp Asp Val Glu Glu Phe Arg Pro Glu Arg Phe Glu Asn Pro Ser Ala
370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
        435                 440                 445
Lys Ser Lys Lys Ile Pro Leu Gly Gly Ile Pro Ser Pro Ser Thr Glu
450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
        515                 520                 525
```

```
Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
        580                 585                 590

Gly Ala Glu Asn Ile Ala Asp Arg Gly Glu Ala Asp Ala Ser Asp Asp
    595                 600                 605

Phe Glu Gly Thr Tyr Glu Glu Trp Arg Glu His Met Trp Ser Asp Val
610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr Asn Val Val Ala Ser Lys Glu Leu
        660                 665                 670

Gln Gln Pro Gly Ser Ala Arg Ser Thr Arg His Leu Glu Ile Glu Leu
    675                 680                 685

Pro Lys Glu Ala Ser Tyr Gln Glu Gly Asp His Leu Gly Val Ile Pro
690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
        740                 745                 750

Val Glu Leu Gln Asp Pro Val Thr Arg Thr Gln Leu Arg Ala Met Ala
    755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
        820                 825                 830

Ser Ser Pro Arg Val Asp Glu Lys Gln Ala Ser Ile Thr Val Ser Val
    835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
        900                 905                 910

Phe Val Gln Ala Arg Lys Gln Leu Lys Glu Gln Gly Gln Ser Leu Gly
    915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
```

-continued

```
             945                 950                 955                 960
His Thr Ala Phe Ser Arg Met Pro Asn Gln Pro Lys Thr Tyr Val Gln
             965                 970                 975
His Val Met Glu Gln Asp Gly Lys Lys Leu Ile Glu Leu Leu Asp Gln
             980                 985                 990
Gly Ala His Phe Tyr Ile Cys Gly Asp Gly Ser Gln Met Ala Pro Ala
             995                1000                1005
Val Glu Ala Thr Leu Met Lys Ser Tyr Ala Asp Val His Gln Val Ser
            1010                1015                1020
Glu Ala Asp Ala Arg Leu Trp Leu Gln Gln Leu Glu Glu Lys Gly Arg
1025                1030                1035                1040
Tyr Ala Lys Asp Val Trp Ala Gly
            1045
```

<210> SEQ ID NO 3
<211> LENGTH: 30
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..30
<223> OTHER INFORMATION: n is a or g or c or t/u, unknown, or other

<400> SEQUENCE: 3
gcaggagacg ggttgnnnac aagctggacg                                       30

<210> SEQ ID NO 4
<211> LENGTH: 30
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..30
<223> OTHER INFORMATION: n is a or g or c or t/u, unknown, or other

<400> SEQUENCE: 4
cgtccagctt gtnnncaacc cgtctcctgc                                       30

<210> SEQ ID NO 5
<211> LENGTH: 34
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..34
<223> OTHER INFORMATION: n is a or g or c or t/u, unknown, or other

<400> SEQUENCE: 5
gaagcaatga acaagnnnca gcgagcaaat ccag                                  34

<210> SEQ ID NO 6
<211> LENGTH: 34
<212> TYPE: DNA
<213> ORGANISM: Artificial sequence
<220> FEATURE:
<223> OTHER INFORMATION: Description of the artificial sequence: PCR
      primer

```
<220> FEATURE:
<221> NAME/KEY: unsure
<222> LOCATION: 1..34
<223> OTHER INFORMATION: n is a or g or c or t/u, unknown, or other

<400> SEQUENCE: 6
ctggatttgc tcgctgnnnc ttgttcattg cttc                                    34

<210> SEQ ID NO 7
<211> LENGTH: 41
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..41
<223> OTHER INFORMATION: n is a or g or c or t/u, unknown, or other

<400> SEQUENCE: 7
gctttgataa aaacttaaag tcaannnctt aaatttgtac g                            41

<210> SEQ ID NO 8
<211> LENGTH: 40
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..40
<223> OTHER INFORMATION: n is a or g or c or t/u, unknown, or other

<400> SEQUENCE: 8
cgtacaaatt taagnnnttg acttaagttt ttatcaaagc                              40

<210> SEQ ID NO 9
<211> LENGTH: 37
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..37
<223> OTHER INFORMATION: n is a or g or c or t/u, unknown, or other

<400> SEQUENCE: 9
gttattaaac acagataaan nngttcaagc tttgatg                                 37

<210> SEQ ID NO 10
<211> LENGTH: 37
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..37
<223> OTHER INFORMATION: n is a or g or c or t/u, unknown, or other

<400> SEQUENCE: 10
catcaaagct tgaacnnntt tatctgtgtt taataac                                 37

<210> SEQ ID NO 11
```

```
<211> LENGTH: 37
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..37
<223> OTHER INFORMATION: n is a or g or c or t/u, unknown, or other

<400> SEQUENCE: 11
gttattaaac acagataaac cgnnncaagc tttgatg                                37

<210> SEQ ID NO 12
<211> LENGTH: 37
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..37
<223> OTHER INFORMATION: n is a or g or c or t/u, unknown, or other

<400> SEQUENCE: 12
catcaaagct tgnnncggtt tatctgtgtt taataac                                37

<210> SEQ ID NO 13
<211> LENGTH: 33
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..33
<223> OTHER INFORMATION: n is a or g or c or t/u, unknown, or other

<400> SEQUENCE: 13
cgaggcgcct ggtnnngtaa cgcgctactt atc                                    33

<210> SEQ ID NO 14
<211> LENGTH: 33
<212> TYPE: DNA
<213> ORGANISM: Artificial sequence
<220> FEATURE:
<223> OTHER INFORMATION: Description of the artificial sequence:
      PCR-primer
<220> FEATURE:
<221> NAME/KEY: unsure
<222> LOCATION: 1..33
<223> OTHER INFORMATION: n is a or g or c or t/u, unknown, or other

<400> SEQUENCE: 14
gataagtagc gcgttacnnn accaggcgcc tcg                                    33

<210> SEQ ID NO 15
<211> LENGTH: 34
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..34
<223> OTHER INFORMATION: n is a or g or c or t/u, unknown, or other
```

```
<400> SEQUENCE: 15
cctggtcgtg taacgcgcnn nttatcaagt cagc                                34

<210> SEQ ID NO 16
<211> LENGTH: 34
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..34
<223> OTHER INFORMATION: n is a or g or c or t/u, unknown, or other

<400> SEQUENCE: 16
gctgacttga taannngcgc gttacacgac cagg                                34

<210> SEQ ID NO 17
<211> LENGTH: 40
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..40
<223> OTHER INFORMATION: n is a or g or c or t/u, unknown, or other

<400> SEQUENCE: 17
gctttgataa aaacttannn caagcgctta aatttgtacg                          40

<210> SEQ ID NO 18
<211> LENGTH: 40
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..40
<223> OTHER INFORMATION: n is a or g or c or t/u, unknown, or other

<400> SEQUENCE: 18
cgtacaaatt taagcgcttg nnntaagttt ttatcaaagc                          40

<210> SEQ ID NO 19
<211> LENGTH: 30
<212> TYPE: DNA
<213> ORGANISM: Artificial sequence
<220> FEATURE:
<223> OTHER INFORMATION: Description of the artificial sequence: PCR
      primer
<220> FEATURE:
<221> NAME/KEY: unsure
<222> LOCATION: 1..30
<223> OTHER INFORMATION: n is a or g or c or t/u, unknown, or other

<400> SEQUENCE: 19
ggcgacgaac tannngttct gattcctcag                                     30

<210> SEQ ID NO 20
<211> LENGTH: 30
<212> TYPE: DNA
<213> ORGANISM: Artificial sequence
<220> FEATURE:
<223> OTHER INFORMATION: Description of the artificial sequence: PCR
```

```
        primer
<220> FEATURE:
<221> NAME/KEY: unsure
<222> LOCATION: 1..30
<223> OTHER INFORMATION: n is a or g or c or t/u, unknown, or other

<400> SEQUENCE: 20
ctgaggaatc agaacnnnta gttcgtcgcc                                          30
```